(12) United States Patent
Tjioe

(10) Patent No.: US 6,579,980 B2
(45) Date of Patent: Jun. 17, 2003

(54) METHOD FOR PREPARING MELAMINE

(75) Inventor: Tjay T Tjioe, Sittard (NL)

(73) Assignee: DSM N.V., Herleen (NL)

( * ) Notice: Subject to any disclaimer, the term of this patent is extended or adjusted under 35 U.S.C. 154(b) by 0 days.

(21) Appl. No.: 09/946,558

(22) Filed: Sep. 6, 2001

(65) Prior Publication Data

US 2002/0007061 A1 Jan. 17, 2002

Related U.S. Application Data

(63) Continuation of application No. PCT/NL00/00129, filed on Mar. 2, 2000.

(30) Foreign Application Priority Data

Mar. 8, 1999 (EP) ............................................. 99200675

(51) Int. Cl.$^7$ ............................................. C07D 251/62
(52) U.S. Cl. ...................................... 544/201; 544/203
(58) Field of Search ................................. 544/201, 203

(56) References Cited

U.S. PATENT DOCUMENTS 5,721,363 A   2/1998   Canzi et al. ................ 544/201
5,731,437 A   3/1998   Turunen et al. ............. 544/201

FOREIGN PATENT DOCUMENTS

| EP | 0747368 | 12/1996 |
|---|---|---|
| EP | 0808836 | 11/1997 |
| WO | 9734879 | 9/1997 |
| WO | 9747609 | 12/1997 |
| WO | 9852928 | 11/1998 |
| WO | 9854160 | 12/1998 |
| WO | 9855466 | 12/1998 |

*Primary Examiner*—Richard L. Raymond
*Assistant Examiner*—Venkataraman Balasubramanian
(74) *Attorney, Agent, or Firm*—Pillsbury Winthrop LLP

(57) ABSTRACT

Method for preparing melamine from urea via a high-pressure process in which solid melamine is obtained by transferring the melamine melt to an expansion vessel where the melamine melt is cooled by incorporated ammonia. Excess ammonia gas is added to the melamine melt to produce a gas/liquid mixture having a mass ratio of at least 0.01. This two-phase mixture is then sprayed via a spraying means into an expansion vessel, the expansion vessel having an ammonia environment with a reduced ammonia pressure. The melamine melt is cooled and solidified by the expansion and evaporation of the incorporated ammonia to form melamine powder. The melamine melt is thereby directly converted into a melamine powder after which the melamine powder is cooled further and the ammonia pressure is released.

15 Claims, No Drawings

METHOD FOR PREPARING MELAMINE

CROSS-REFERENCE TO RELATED APPLICATIONS

This Application is a continuation of International Application PCT/NL00/00129, filed Mar. 2, 2000, which designated the U.S. and was published in the English language.

The invention relates to a method for preparing melamine from urea via a high-pressure process in which solid melamine is obtained by transferring a melamine melt to a vessel where it is cooled with a cooling medium such as ammonia to produce solid high purity melamine.

Various methods for the production of melamine have been described in previous publications including, inter alia, EP-A-747366 which describes a high-pressure process for preparing melamine from urea. In particular, EP-A-747366 describes how urea is pyrolyzed in a reactor, operating at a pressure of from 10.34 to 24.13 MPa and a temperature of from 354 to 454° C., to produce a reactor product. This reactor product, containing liquid melamine, $CO_2$ and $NH_3$, is transferred under pressure as a mixed stream to a separator.

In this separator, the reactor product is separated into a gaseous stream and a liquid stream. The gaseous stream contains primarily $CO_2$ and $NH_3$ waste gases and melamine vapor. The liquid stream mainly comprises a melamine melt. The gaseous stream is transferred to a scrubber unit, while the liquid stream is transferred to a product-cooling unit.

In the scrubber unit, the gaseous stream is scrubbed with molten urea. The heat transfer achieved in the scrubber unit both preheats the molten urea and cools the gaseous stream to a temperature from 177 to 232° C. The molten urea also scrubs the gaseous stream to remove the melamine vapor from the waste gases. The preheated molten urea, along with the melamine that was scrubbed from the $CO_2$ and $NH_3$ waste gases, is then fed into the reactor.

In the product-cooling unit, the melamine melt is cooled and solidified with a liquid cooling medium to produce a solid high purity melamine product without the need for additional purification. The preferred liquid cooling medium is one that forms a gas at the temperature of the melamine melt and at the pressure in the product-cooling unit. EP-A-747366 identifies liquid ammonia as the preferred liquid cooling medium with the pressure in the product-cooling unit being above 4.14 MPa.

Although according to EP-A-747366 the purity of the solid melamine product obtained using the disclosed process was greater than 99 wt %, this degree of purity has proven difficult to maintain continuously on a commercial scale. The inability to maintain a purity greater than 99 wt % is a drawback that renders the melamine produced less suitable for more demanding applications, particularly melamine-formaldehyde resins used in laminates and/or coatings.

Other methods have been suggested to overcome these drawbacks, including among them the applicant's earlier application, WO 98/55466, which used an external spray of liquid ammonia or cool ammonia gas spray to cool the melamine melt, which may be mixed with a minor amount of ammonia gas, as it was sprayed into the cooling vessel. Although this method represented a significant improvement over the prior art methods, the method described in WO 98/55466 still required an external spray of a cooling medium to solidify the melamine. The most efficient cooling of the melamine melt with an external spray, however, depends upon thorough atomization of the melamine melt (to maximize surface area) and thorough mixing of the atomized melamine melt and the cooling medium spray. A lack of uniformity in the melamine droplet size or spray pattern, and/or non-homogeneous mixing of the droplets and the cooling medium will produce less than optimum results.

Yet another method is taught in WO 97/20826 which provides for the solidifaction of the melamine through expansion and evaporation of dissolved ammonia. WO 97/20826 teaches the use of relatively high pressures, up to 40 MPa, at temperatures up to 60° C. above the melting point of melamine, followed by expansion of the melamine melt at a pressure between 20 MPa and amospheric pressure. In order to get a quantity of ammonia into solution sufficient to provide the desired cooling, the initial pressures are preferably high and the pressure drop during the relaxation step is large. In general, however, using higher pressures in a commercial plant necessitates increased capital investment in process vessels, piping, and pumps, and results in higher operating costs. It is preferable, therefore, to operate at the lowest possible pressure at which satisfactory results may be obtained.

The object of the present invention is to provide an improved method for preparing melamine from urea, in which melamine is obtained directly from liquid melamine melt as a dry powder having a high degree of purity. More particularly, the object of the present invention is to obtain an improved high-pressure process for preparing melamine from urea, in which melamine is obtained directly from the liquid melamine melt as a dry powder having a high degree of purity by cooling and solidifying via an incorporated cooling medium.

The applicant has found that high purity melamine can be produced from the melamine melt, which has a temperature between the melting point of melamine and 450° C., preferably less than 45° C., and more preferably less than 30° C. above the melting point, by incorporating sufficient excess ammonia into the melamine melt in an ammonia injection vessel to form a gas/liquid mixture having a gas/liquid mass ratio between 0.01 and 1.0, and preferably between 0.03 and 0.9. This gas/liquid mixture is then sprayed via a spraying means into an expansion vessel to cool and solidify the melamine by expanding and evaporating the incorporated ammonia in the reduced pressure expansion vessel. The expansion vessel includes an ammonia atmosphere that, although preferably held at a pressure between 0.5% and 60% of the pressure of the ammonia injection vessel, more preferably between 0.5% and 30% of the pressure of the ammonia injection vessel, is still above atmospheric pressure. The melamine powder thereby obtained may then be cooled further in the expansion vessel, or in a separate cooling vessel, and the pressure reduced to atmospheric pressure to obtain the final melamine powder product.

In the ammonia injection vessel, ammonia is injected into the melamine melt, the quantity of ammonia injected being more than necessary to saturate the melamine melt at equilibrium. The excess ammonia is maintained in the melamine melt as ammonia bubbles, the melamine melt and ammonia bubbles forming a two-phase gas/liquid mixture.

In the expansion vessel, the gas/liquid mixture is rapidly decompressed to cool and solidify the molten melamine. The expansion and vaporization of the excess ammonia in the gas/liquid mixture is sufficient to solidify the melamine without the need for any external cooling medium such as gas or liquid ammonia sprays, aqueous ammonia solutions, or other cooling means. Further cooling of the solid melamine may, however, be desirable and may be achieved by applying various techniques as disclosed in the prior art, particularly through the introduction of liquid ammonia or cool ammonia gas into the solid melamine.

The advantage of the method according to the present invention is the continuous production, on a commercial scale, of dry melamine powder with a purity above 98.5 wt %, and generally above 99 wt %, that has very good color characteristics. The high purity melamine produced according to the present invention is suitable for virtually any melamine application, including melamine-formaldehyde resins used in laminates and/or coatings. At similar operating conditions, the melamine powder produced according to the present invention provides other advantages over the melamine produced by the prior art processes including reduced particle size, increased surface area, and increased porosity.

The preparation of melamine preferably uses urea as the raw material, the urea being fed into the reactor as a melt and reacted at elevated temperature and pressure. Urea reacts to form melamine, and the by-products $NH_3$ and $CO_2$, according to the following reaction equation:

6 $CO(NH_2)_2$ ® $C_3N_6H_6$+6 $NH_3$+3 $CO_2$

The production of melamine from urea can be carried out at high pressure, preferably between 5 and 25 MPa, without the presence of a catalyst, at reaction temperatures between 325 and 450° C., and preferably between 350 and 425° C. The by-products $NH_3$ and $CO_2$ are usually recycled to an adjoining urea factory.

The above-mentioned objective of the invention is achieved by employing an apparatus suitable for the preparation of melamine from urea. An apparatus suitable for the present invention may comprise a scrubber unit, a reactor having either an integrated gas/liquid separator or a separate gas/liquid separator, an ammonia injection vessel, an expansion vessel, and possibly additional cooling vessels. It will be appreciated that the configuration of the ammonia injection vessel is not restricted and may, depending on the plant configuration, comprise a portion of the piping between the reactor, or the gas/liquid separator, and the expansion vessel.

In one embodiment of the invention, melamine is prepared from urea in an apparatus comprising a scrubber unit, a melamine reactor having either an integrated gas/liquid separator or a separate gas/liquid separator, an ammonia injection vessel, an expansion vessel, and an optional cooling vessel. In this embodiment, the urea melt is fed into a scrubber unit operating at a pressure of from 5 to 25 MPa, preferably from 8 to 20 MPa, and at a temperature above the melting point of urea. This scrubber unit may be provided with a cooling jacket or internal cooling bodies to provide additional temperature control.

As it passes through the scrubber unit, the urea melt contacts the reaction waste gases coming from the melamine reactor or the separate gas/liquid separator. The reaction gases mainly consist of $CO_2$ and $NH_3$ and may include melamine vapor. The urea melt scrubs the melamine vapor from the $CO_2$ and $NH_3$ waste gases and carries this melamine along back to the reactor. In the scrubbing process, the waste gases are cooled from the temperature of the reactor, i.e., from 350 to 425° C., to from 170 to 240° C., the urea being heated to from 170 to 240° C. The $CO_2$ and $NH_3$ waste gases are removed from the top of the scrubber unit and may, for example, be recycled to an adjoining urea factory, where they can be used as raw materials for the urea production.

The preheated urea melt is drawn off from the scrubber unit, together with the melamine scrubbed from the waste gases, and transferred to the high pressure reactor operating at pressures between 5 and 25 MPa, and preferably between 8 and 20 MPa. This transfer may be achieved using a high-pressure pump or, where the scrubber is positioned above the reactor, by gravity, or a combination of gravity and pumps.

In the reactor, the urea melt is heated to a temperature between 325 and 450° C., preferably between about 350 and 425° C., under a pressure between 5 and 25 MPa, preferably between 8 and 20 MPa, to convert the urea into melamine, $CO_2$ and $NH_3$. In addition to the urea melt, a certain amount of ammonia can be metered into the reactor as, for example, a liquid or hot vapor. The additional ammonia, although optional, may serve, for example, to prevent the formation of condensation products of melamine such as melam, melem and melon, or to promote mixing in the reactor. The amount of additional ammonia supplied to the reactor may be up to 10 moles ammonia per mole of urea, preferably up to 5 moles ammonia per mole of urea, and, most preferably, up to 2 moles of ammonia per mole of urea.

The $CO_2$ and $NH_3$ produced in the reaction, as well as any additional ammonia supplied, collect in the separation section, for example in the top of the reactor or in a separate gas/liquid separator positioned downstream of the reactor, and are separated from the liquid melamine. If a separate, downstream gas/liquid separator is used, it may be advantageous for additional ammonia to be metered into this separator. The amount of ammonia in this case is 0.01–10 moles of ammonia per mole of melamine, and preferably 0.1–5 moles of ammonia per mole of melamine. Adding additional ammonia to the separator promotes the rapid separation of carbon dioxide from the reactor product, thus preventing the formation of oxygen-containing by-products. As described above, the gas mixture removed from the gas/liquid separator may be passed to the scrubber unit in order to remove melamine vapor and preheat the urea melt.

The melamine melt, having a temperature between the melting point of melamine and 450° C., is drawn off from the reactor, or from the downstream gas/liquid separator, and optionally cooled, is then fed into an ammonia injection vessel. In the ammonia injection vessel, excess ammonia is added to the melamine melt to produce a gas/liquid mixture in which ammonia is present both in solution and as a separate gas phase. Sufficient ammonia is added to produce a two-phase stream in which the gas/liquid mass ratio is between 0.01 and 1.0, and preferably between 0.03 and 0.9. This gas/liquid mixture is then sprayed into an expansion vessel to obtain the solid melamine product.

Prior to spraying in the expansion vessel, however, the melamine melt may be cooled from the reactor temperature or gas/liquid separator temperature to a temperature closer to, but still above, the melting point of melamine. The melamine melt, which is drawn off from the reactor at a temperature typically above 380° C., may be cooled to a temperature preferably not more than 45° C., and more preferably not more than 30° C., above the melamine melting point before being sprayed into the expansion vessel. The lower the temperature of the melt before expansion, the lesser ammonia is needed for cooling and solidifying the melamine melt in the expansion vessel. The melamine melt may be cooled in the gas/liquid separator, the ammonia injection vessel, or in an additional apparatus positioned downstream from the reactor and before the expansion vessel. It is contemplated that cooling can take place by injection of a cooling medium, for example ammonia gas having a temperature below the temperature of the melamine melt, or by passing the melamine melt through a heat exchanger.

The melamine and ammonia mixture, is transferred to a spraying means as a two-phase mixture and there it is sprayed through a spraying means into an expansion vessel to solidify the melamine and form a dry melamine powder. The spraying means is an apparatus by which the gas/liquid mixture is converted into droplets, by causing the melt to flow at high speed into the expansion vessel. The spraying means may be a nozzle or valve. The outflow velocity of the gas/liquid mixture from the spraying means is, as a rule, greater than 20 m/s, and is preferably greater than 50 m/s. The outflow velocity is defined as the nominal volumetric flow of the mixture (in $m^3/s$) devided by the smallest cross sectional flow area in the nozzle or valve (in $m^2$).

The expansion vessel contains an ammonia environment and operates at an increased ammonia pressure. The melamine droplets from the spraying means are cooled by energy transfer from the molten melamine to the expanding and evaporating ammonia to produce melamine powder. The melamine powder thus formed can have a temperature between 100° C. and the solidification point of melamine, and preferably below 300° C.

In another embodiment of the present invention the melamine powder formed by spraying the gas/liquid mixture into the expansion vessel is held in the expansion vessel for a predetermined contact time under an increased ammonia pressure and at a temperature above 200° C. The duration of this contact time is preferably between 5 minutes and 2 hours. During this contact time, the temperature of the melamine product can remain virtually constant or it may be cooled to a temperature above 200° C. Additional cooling of the solidified melamine may be effected through the addition of cool ammonia gas or liquid ammonia, separately or in combination with mechanical agitation and indirect cooling through contact with cooled surfaces. Examples of means for mechanically agitating the melamine powder include a screw and rotating drum, a rotating bowl, rotating discs, rotating segmented discs, rotating pipes and the like.

Once the melamine powder has been cooled to a temperature below 200° C., the ammonia pressure may be released. Preferably, the ammonia gas is completely removed (to an amount below 1000 ppm, preferably below 300 ppm, and, most preferably, below 100 ppm) by blowing air through the melamine powder. The ammonia pressure may be released before, or in conjunction with, cooling the melamine powder from a temperature below 200° C. to ambient temperature.

The invention will be explained in more detail with reference to the following examples and comparative examples.

EXAMPLE I

To a melamine melt, which is saturated with ammonia at a temperature of 359° C. and a pressure of 20.4 MPa, additional ammonia gas with the same temperature is added. The liquid flow is 4.8 kg/hour and the additional ammonia gas flow is 1.4 kg/hour. This two-phase flow is depressurized in a vessel wherein an ammonia pressure of 2.5 MPa is maintained, resulting in solidification of the melamine melt. The melamine melt is further cooled with liquid ammonia and the vessel is depressurized. The product has a melamine purity of 99.6%.

EXAMPLE II

To a melamine melt, which is saturated with ammonia at a temperature of 353° C. and a pressure of 17.9 MPa, additional ammonia gas with the same temperature is added. The liquid flow is 4.8 kg/hour and the additional ammonia gas flow is 0.9 kg/hour. This two-phase flow is depressurized in a vessel with an ammomia pressure of 1.8 MPa, resulting in solidification of the melamine melt. The melamine melt is further cooled with liquid ammonia and the vessel is depressurized. The product has a melamine purity of 99.2%.

COMPARATIVE EXAMPLE A

The same experiment as mentioned in example I is performed without the additional ammonia gas flow. So only a single phase melamine melt is depressurized in the quench vessel. The product has a melamine purity of 98.7%.

COMPARATIVE EXAMPLE B

The same experiment as mentioned in example II is performed without the additional ammonia gas flow. So only a single phase melamine melt is depressurized in the quench vessel. The product has a melamine purity of 98.5%.

What is claimed is:

1. A method for preparing melamine having high purity from a melamine melt, said method comprising:

introducing melamine melt at a temperature of from the melting point of melamine to 450° C. into an injection vessel;

introducing a quantity of ammonia into the injection vessel in an amount which is in excess of the equilibrium saturation amount relative to the molten melamine to thereby form a two-phase gas/liquid mixture wherein ammonia is present in the mixture dissolved in the melamine melt and in the form of gas bubbles, the gas/liquid mixture having a gas/liquid mass ratio of from 0.01 to 1.0, and spraying the two-phase gas/liquid mixture into an expansion vessel having an ammonia atmosphere at a lower pressure than the pressure in the injection vessel but above atmospheric pressure, whereby directly causing the gaseous ammonia in the mixture to expand and evaporate and thereby cooling and solidifying the liquid melamine without requiring additional or external cooling.

2. Method according to claim 1, wherein the gas/liquid mass ratio is between 0.03 and 0.9.

3. Method according to claim 1, wherein the temperature of the melamine melt being sprayed into the expansion vessel is between the melting point of melamine and a temperature 45° C. above the melting point of melamine.

4. Method according to claim 1, wherein the temperature of the melamine melt being sprayed into the expansion vessel is between the melting point of melamine and a temperature 30° C. above the melting point of melamine.

5. Method according to claim 1, wherein the expansion vessel includes an ammonia pressure held between 0.5% and 60% of the pressure of the injection vessel.

6. Method according to claim 1, wherein the expansion vessel includes an ammonia pressure held between 0.5% and 30% of the pressure of the injection vessel.

7. Method according to claim 1, wherein the configuration of the injection vessel comprises a portion of piping between a reactor for the production of the melamine melt or a gas/liquid separator for the production of the melamine melt and the expansion vessel.

8. Method according to claim 1, wherein the outflow velocity of the gas/liquid mixture being sprayed into the expansion vessel is greater than 50 m/sec.

9. Method according to claim 1, which further comprises further lowering the temperature of the solidified melamine and releasing the ammonia pressure when the solidified melamine has a temperature below 200° C.

10. The process according to claim 1, wherein the melamine melt is a melt prepared from urea via a high-pressure process.

11. The process according to claim 10, wherein the high-pressure process comprises reacting molten urea at a reaction temperature between 325 and 450° C. and at an elevated pressure between 5 and 25 MPa to produce a reaction mixture comprising melamine, ammonia and carbon dioxide and separating ammonia and carbon dioxide from the reaction mixture in a gas/liquid separator, and wherein the configuration of the injection vessel comprises a portion of piping between the reactor or the gas/liquid separator and the expansion vessel.

12. The process according to claim 10, wherein the melamine melt from the high-pressure process has a temperature above 380° C., said process further comprising cooling the melamine melt to a temperature below 380° C. before introducing the melt into the evaporation vessel.

13. The process according to claim 1, further comprising introducing liquid ammonia into the solidified liquid melamine.

14. The process according to claim 1, further comprising introducing ammonia gas at a temperature below the temperature of the solidified liquid melamine, into the solidified liquid melamine.

15. The process according to claim 1, which is carried out continuously.

* * * * *

UNITED STATES PATENT AND TRADEMARK OFFICE
CERTIFICATE OF CORRECTION

PATENT NO.      : 6,579,980 B2
DATED           : June 17, 2003
INVENTOR(S)     : Tjioe It is certified that error appears in the above-identified patent and that said Letters Patent is hereby corrected as shown below:

<u>Title page,</u>
Item [73], please correct the Assignee information to read:

-- [73]  Assignee:  DSM N.V., Heerlen (NL) --

Signed and Sealed this

Ninth Day of December, 2003

JAMES E. ROGAN
*Director of the United States Patent and Trademark Office*